US006816256B1

(12) United States Patent
Lloyd

(10) Patent No.: US 6,816,256 B1
(45) Date of Patent: Nov. 9, 2004

(54) RESPONSE ASSESSMENT

(75) Inventor: Christopher J. Lloyd, Manchester (GB)

(73) Assignee: The Victoria University of Manchester, Manchester (GB)

(*) Notice: Subject to any disclaimer, the term of this patent is extended or adjusted under 35 U.S.C. 154(b) by 0 days.

(21) Appl. No.: 09/720,358

(22) PCT Filed: Jun. 24, 1999

(86) PCT No.: PCT/GB99/01989

§ 371 (c)(1),
(2), (4) Date: Feb. 15, 2001

(87) PCT Pub. No.: WO99/67622

PCT Pub. Date: Dec. 29, 1999

(30) Foreign Application Priority Data

Jun. 25, 1998 (GB) .............................. 9813613

(51) Int. Cl.[7] .............................. G01J 3/30; G01J 3/52; G01J 1/58
(52) U.S. Cl. ..................... 356/317; 356/417; 250/458.1; 250/459.1
(58) Field of Search ................................ 356/317, 417; 436/172; 422/82.05, 82.08; 250/458.1, 459.1, 461.1, 461.2

(56) References Cited

U.S. PATENT DOCUMENTS

| | | | | | |
|---|---|---|---|---|---|
| 4,437,772 | A | * | 3/1984 | Samulski | 374/129 |
| 5,304,809 | A | * | 4/1994 | Wickersheim | 250/458.1 |
| 5,426,306 | A | * | 6/1995 | Kolber et al. | 250/458.1 |
| 5,828,452 | A | * | 10/1998 | Gillispie et al. | 356/328 |
| 5,909,278 | A | * | 6/1999 | Deka et al. | 356/318 |
| 5,955,737 | A | * | 9/1999 | Hallidy et al. | 250/458.1 |
| 6,121,053 | A | * | 9/2000 | Kolber et al. | 436/172 |
| 6,137,584 | A | * | 10/2000 | Seidel et al. | 356/445 |
| 6,515,289 | B1 | * | 2/2003 | Kask | 250/459.1 |
| 6,556,296 | B1 | * | 4/2003 | Palo | 356/317 |

FOREIGN PATENT DOCUMENTS

| | | | |
|---|---|---|---|
| WO | WO 85/03352 | 8/1985 | |
| WO | 85/03352 | 8/1985 | |
| WO | WO 9823941 A2 * | 6/1998 | ........ G01N/15/02 |
| WO | 99/21063 | 4/1999 | |
| WO | WO 99/21063 | 4/1999 | |

OTHER PUBLICATIONS

Palo, Kaupo; Sep. 1997; U.S. Provisional Application 60/060344.*

Legendre et al, "An All Solid–State Near–Infrared Time–Correlated Single Photon Counting Instrument for Dynamic Lifetime Measurements in DNA Sequencing Applications", Review of Scientific Instruments, vol. 67, No. 11, Nov. 1, 1996, pp. 3984–3989, XP000635855.

Becker W et al.: "Flexible Instrument for Time–Correlated Single–Photon Counting" Review of Scientific Instruments, vol. 62, No. 12, Dec. 1991, pp. 2991–2996.

* cited by examiner

*Primary Examiner*—Zandra V. Smith
*Assistant Examiner*—Gordon J. Stock, Jr.
(74) *Attorney, Agent, or Firm*—Nixon & Vanderhye P.C.

(57) ABSTRACT

A characteristic response of a medium to an excitation transient of predetermined duration which causes the medium to emit a series of signals over a period of time which is long relative to the duration of the excitation transient is assessed. The signals are detected and the duration of each interval between successive signals is measured. A relationship relating the interval between the excitation transient and the emission of each signal to the interval between each signal and the preceding signal in the series is derived to represent the characteristic response.

15 Claims, 2 Drawing Sheets

RESPONSE ASSESSMENT

BACKGROUND OF THE INVENTION

1. Field of the Invention

The present invention relates to a method and apparatus for assessing the characteristic response of a medium to an excitation transient which causes the medium to emit a series of signals over a period of time which is long compared to the duration of the excitation transient.

The present invention is particularly applicable to the assessment of a fluorescent decay but could be applied to any circumstances in which an excitation triggers a response that has decay or other time dependent characteristics which continue for a substantial period of time after termination of the excitation. The nature of the excitation may be the same as or different from the nature of the emission, for example light trigger and light emission or chemical trigger and light emission, and the excited species need not be excited directly, for example excimer and fluorescence energy transfer where the excited species is not the emitting species.

2. Description of Related Art

In conventional fluorescence decay analysis, in which a series of photons are emitted after pulse excitation, the time interval between the excitation pulse and the first emitted photon is monitored. The sample is repeatedly excited to enable the accumulation of data representing the distribution of the arrival times of the first photons resulting from each excitation. A significant delay is required between successive excitations to ensure that aliasing does not occur, that is to ensure that a photon emission resulting from one excitation is not detected as the first emitted photon resulted from the next excitation. Typically the delay required is from 10 to 100 times the fluorescent lifetime. These delays, coupled with the need for repeated excitation, prevent high speed measurements being obtained.

A further disadvantage of conventional fluorescence detection methods is that the intensity of successive excitation pulses may vary. This variation of excitation pulse intensity will cause distortion of the measured fluorescent lifetime. The distortion is particularly pronounced if the excitation mechanism is non linear, for example two-photon absorption.

The distortion may be reduced by stabilising the source of the excitation pulses. However, such stabilisation will not fully remove intensity variation between successive excitation pulses.

The effect of excitation pulse intensity variation is often reduced using normalisation. Normalisation involves modifying the statistical significance of a detected fluorescence photon according to the intensity of the corresponding excitation pulse. A disadvantage of normalisation is that it requires high speed electronics. Furthermore, where the normalisation involves recording the intensity of the excitation pulse, the amount of data which must be stored during a measurement is significantly increased. This is because the intensity of the excitation pulse will typically be represented by 12 or more bits, whereas the detected fluorescence photon be represented by a single bit.

BRIEF SUMMARY OF THE INVENTION

It is an object of the present invention to obviate or mitigate at least some of the problems outlined above.

According to the present invention, there is provided a method for assessing the characteristic response of a medium to an excitation transient of predetermined duration which causes the medium to emit a series of signals over a period of time which is long relative to the duration of the excitation transient, wherein the signals are detected, the duration of each interval between successive signals is measured, and a relationship relating the interval between the excitation transient and the emission of each signal to the interval between each signal and the preceding signal in the series is derived to represent the characteristic response.

Preferably the interval between the excitation transient and the emission of each signal is plotted against the interval between each signal and the preceding signal in the series, a curve is fitted to the plot, the position of the minimum value of the interval between the excitation transient and the emission of each signal as represented by the curve is determined, and the interval between successive signals corresponding to the position of the minimum is determined to provide a measure of the characteristic response of the medium.

The excitation transient may be a short pulse (i.e. shorter than the duration of the characteristic response to be measured). Alternatively the excitation may be a long pulse which provides a steady state of excitation, the excitation transient being a rapidly decaying falling edge of the long pulse. In a further alternative, the excitation may be a two-photon excitation, obtained via two excitation sources, in which case the excitation transient is the period during which both sources excite the medium simultaneously.

The present invention makes it possible to measure for example a fluorescent decay lifetime from pulse (quantum) signals resulting from only a single excitation transient of very short duration, for example a few nanoseconds, or less.

The invention is advantageous because it reduces the effect of variation of the excitation intensity.

The invention allows the characteristic response of the medium to be assessed from a single excitation transient.

The invention also allows the measurement of a characteristic response from a series of excitations of a medium, i.e. by averaging the lifetimes measured in response to a series of excitations. Intensity variations between successive excitations will not distort the measured fluorescence decay lifetime because the measurement according to the invention is unaffected by intensity variations. Therefore, no normalization is required.

Where normalisation is used, for example where the quantity of a fluorescent medium is to be determined, the amount of data that must be stored to perform the normalisation is small because the intensity of each excitation may be used to normalise the series of detected fluorescence photons emitted in consequence of that excitation. This compares to the prior art, wherein each detected fluorescence photon must be normalised according to a separate excitation intensity measurement.

The invention is particularly applicable to the analysis of signals resulting from excitation of fluorophores. The signals may result from direct excitation or energy transfer to one species from another species excited by the excitation.

The timing of the signals may be determined from any convenient portion of each signal, for example the leading edge.

A property of the excitation may be used to normalise the detected signals.

A bleaching rate of a fluorophore may be measured. The bleaching rate may be used as a marker to monitor the conformation, environment or binding of the fluorophore.

The invention may be applied to the assessment of a large number of samples of a particular medium using a single source. Excitation may be delivered to the samples from the single source and received by a single detector. Each of the samples may receive an excitation in turn, signals from each of the samples being detected in turn, or alternatively each of the samples may receive an excitation simultaneously, with signals from all of the samples being detected in parallel. This latter approach enables rapid assessment of a large number of samples to determine whether any of them is generating a characteristic response before the application of the first approach to assess individual samples which do exhibit some characteristic response.

BRIEF DESCRIPTION OF THE DRAWINGS

An embodiment of the present invention will now be described, by way of example, with reference to the accompanying drawings, in which.

DETAILED DESCRIPTION OF EXEMPLARY EMBODIMENTS OF THE INVENTION

Figure 1:
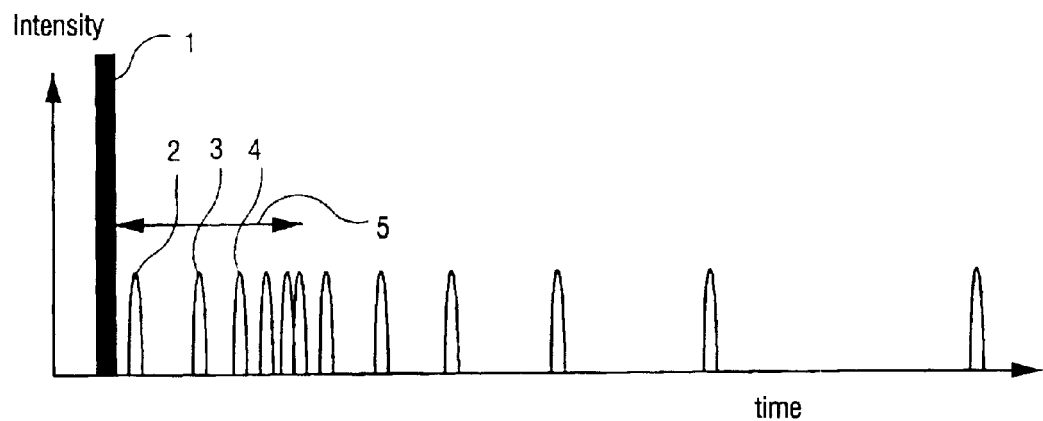
FIG. 1 illustrates the timing of the emission of photons by a fluorescent sample after excitation by a short-duration excitation pulse.

Referring to FIG. 1, this illustrates the excitation of and emissions from a sample which has fluorescent properties having a characteristic lifetime. An excitation pulse 1 is used to excite the sample and as a result a series of photons is emitted, each photon being detected to generate a signal pulse. The first three photons emitted after the excitation pulse 1 are indicated in FIG. 1 by pulses 2, 3 and 4. The arrow 5 in FIG. 1 represents the characteristic lifetime of the excited sample.

Figure 2:
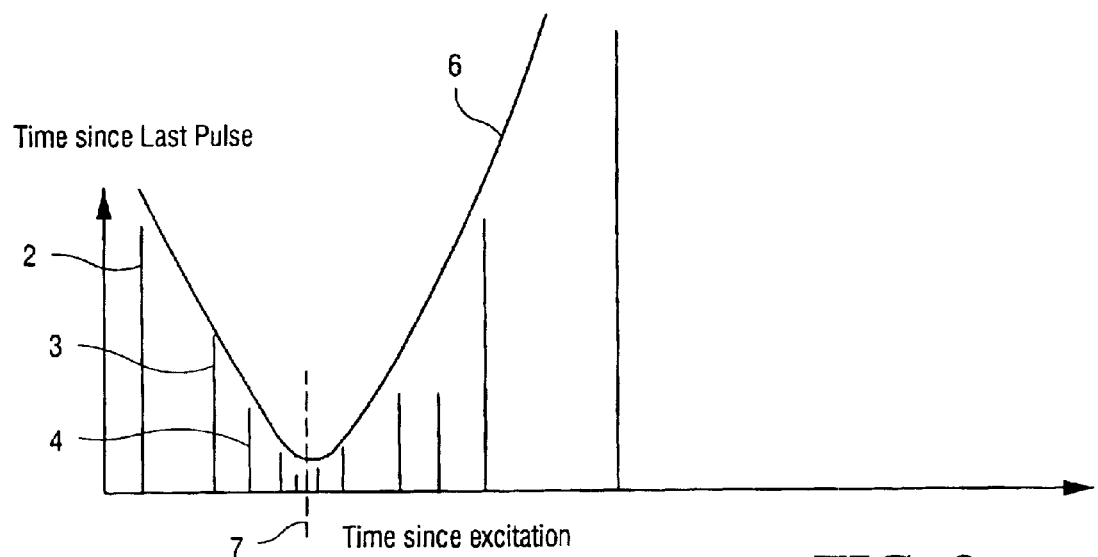
FIG. 2 is a representation of data derived from the events represented in FIG. 1.

Referring to FIG. 2, this represents data extracted from the events represented in FIG. 1. The horizontal axis corresponds to the time interval which has elapsed since excitation when an emission pulse is detected. The lines corresponding to the signal pulses 2, 3 and 4 in FIG. 1 are identified by the same numbers in FIG. 2. The vertical axis corresponds to the time interval which has elapsed since the preceding signal pulse in the series. Thus the length of the line 3 in FIG. 2 corresponds to the time interval between signal pulses 2 and 3 of FIG. 1.

A curve 6 is then fitted to the data represented in FIG. 2 and exhibits a pronounced minimum at the position indicated by line 7 on the "time since excitation" axis. The time interval represented by the position of the line 7 corresponds to the characteristic lifetime of the sample.

Given that the photon emission pulse signals represented in FIG. 1 relate to the decay of an active species, the resulting pulse train will inevitably "bunch" around the characteristic lifetime of that species. Thus although the pulse emission times represented in FIG. 1 may appear to be random for any particular emission pulse, the underlying trend is clear and may be analysed by the simple plotting and curve fitting techniques described with reference to FIG. 2.

In many cases it may not be possible to make the excitation pulse sufficiently narrow that it may be considered to be a delta function. Where this is not possible, the excitation pulse width may be deconvoluted from the detected signal.

In noisy environments, correlation or equivalent signal processing techniques may be applied to the emission signals to increase sensitivity.

The detected pulse train may be normalised. This is done by detecting the intensity of the excitation pulse and then adjusting the statistical significance of the detected pulse train following that excitation pulse, in accordance with the detected excitation pulse intensity. Normalisation techniques are well known in the art, and are generally used to normalise single detected pulses emitted following single excitation pulses. The invention is advantageous because it allows the normalisation of a detected pulse train, rather than just a single detected pulse, using a single excitation pulse intensity measurement. The rate at which excitation pulses must be detected is thereby reduced, allowing slower (and cheaper) electronics to be used, and reducing the amount of memory required to store the intensity of the excitation pulses.

The described approach allows very rapid analysis, for example analysis of the characteristic decay time of a fluorophore in under four decay lifetimes, that is in a timescale significantly below 1 microsecond for most fluorophores.

Although the described embodiment of the invention utilises excitation pulses which are short compared to the characteristic lifetime, other forms of excitation may be used. For example, a long excitation pulse with a rapidly decaying falling edge may be used, the emission signal being timed in relation to the falling edge.

The invention may be applied to mass screening, relying upon multiplexing of the detector and/or emitter as described with reference to FIG. 3.

Figure 3:
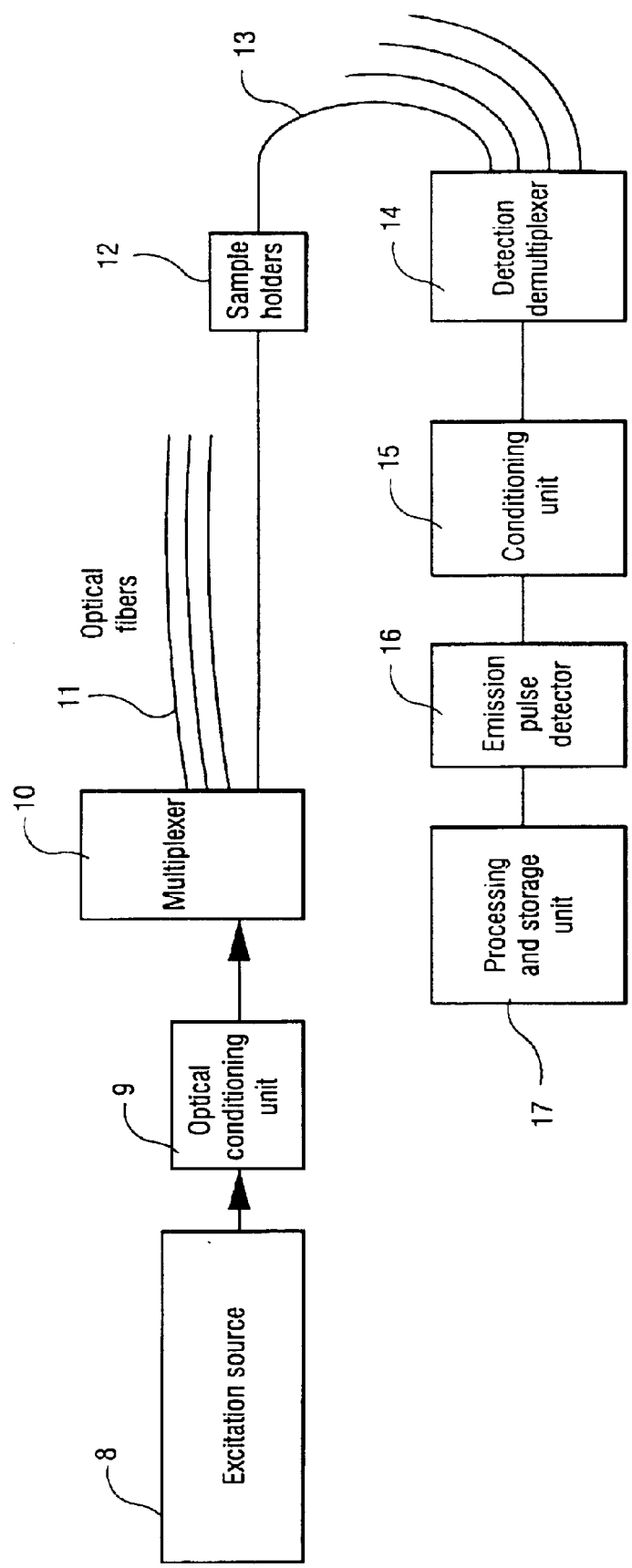
FIG. 3 is a schematic representation of an apparatus in accordance with the present invention.

Referring to FIG. 3, light from a pulsed excitation source 8 is conditioned in an optical conditioning unit 9 which may incorporate for example filters, polarises, lenses etc and delivered to a multiplexer 10 which delivers excitation pulses of light to each of a series of optical fibres 11. Each of the optical fibres 11 delivers light to a respective sample holder 12, only one of the sample holders being shown. Each of the sample holders 12 is coupled by a respective optical fibre 13 to a detection demultiplexer 14 the output of which is applied via a conditioning unit 15 to a emission pulse detector 16. A processing and storage unit 17 is used to convert the detected pulse data which is represented in FIG. 1 into the representation illustrated with reference to FIG. 2.

After each excitation light pulse the light emitted from the illuminated sample is detected and stored. The multiplexers may be switched to deliver light to and receive light from only one sample at a time. Alternatively, light may be delivered to and detected from all of the samples simultaneously. This alternative would allow a first pulse to be sent to each sample in parallel, and if no photon emission signal resulted from any of the samples it would not then be necessary to analyse each of the samples in turn. The process could simply move on to the next array of samples. If however one or more of the individual samples did emit a photon, the system could be switched back to the full multiplex configuration in which an excitation pulse would be delivered to each of the samples in turn. The detection multiplexer would switch to each of the samples in turn to thereby allow assessment of a fresh sample even if the previously assessed sample might still be emitting photons. Any signals emitted by the previously assessed sample would simply not be detected if the demultiplexer had been switched away from that sample.

For fluorophores with lifetimes of 20 nanoseconds or less, the total measurement time for a plate having wells for 96 samples will be less than 1 microsecond per well giving a measurement time for the whole plate of less than 1 millisecond.

The multiplexers may be switchable between true multiplexing and beam splitting configurations. Alternatively the system could be constructed with diffraction pattern generators, scanning devices, mirror assemblies or shutters for example.

Thus the present invention makes it possible to measure the characteristic lifetime of a fluorescent response or other time-dependent response by means of excitation with a single pulse and subsequent timing of the intervals between resultant emitted signals. Signal analysis may include correlation, or equivalent signal processing in real time or after storage. The invention is particularly applicable to fluorescent decay spectroscopy but may be applied in any other media such as radioactive decay or chemical induced decay.

The decay may not be of the triggered species but of a complex (i.e. excimer) or other species which has had energy transfer from another species that has been excited (i.e. fluorescent energy transfer). A selected portion of the emitted signal may be analysed, the remainder of the signal simply being ignored or used as a trigger signal. A multi-channel system may utilise many excitation sources and detectors or only a single excitation source and detector with "channels" being formed by multiplexed fibres, pattern generators or other beam splitting and combining methods.

Generally a single excitation pulse will be used but it may be possible to use multiple excitation pulses with a single sample to measure the "bleaching" of the excited species as a further measurement parameter. The term bleaching is used to indicate a situation in which a fluorescent sample is continuously or repeatedly excited and the intensity of the fluorescent emission reduces due to the effect of that excitation. The bleaching rate of a fluorophore may be used as a means of fluorophore identification. Furthermore, a variation of the bleaching rate of a fluorophore may be used to identify a change in its environment, conformation or binding.

The invention could be applied to single particle detection where the measurement is on an individual particle passing through a flow cell.

It will be understood that, in situations where the excitation pulse width is significant in relation to the measured characteristic response of a medium, the effect of the pulse width may be removed from the measured characteristic response using known techniques. This may be done for example using known de-correlation techniques or Fourier transform analysis.

Any available techniques may be used for detection of the emission signal pulses resulted from sample excitation. One possible approach to signal detection is that described in British patent application number 9721847.3. That specification describes a timing circuit for recording the duration of an interval between two events, the timing circuit comprising a source of clock pulses and a counter which accumulates the clock pulses occurring between the events, the clock and counter being arranged such that the accumulated count increases at a rate which reduces with increasing interval duration.

What is claimed is:

1. A method for assessing the characteristic response of a medium to an excitation transient of predetermined duration which causes the medium to emit a series of signals over a period of time which is long relative to the duration of the excitation transient, wherein the signals are detected, the duration of each interval between successive signals is measured, and a relationship relating the interval between the excitation transient and the emission of each signal to the interval between each signal and the preceding signal in the series is derived to represent the characteristic response;

wherein the interval between the excitation transient and the emission of each signal is plotted against the interval between each signal and the preceding signal in the series, a curve is fitted to the plot, the position of a minimum value of the interval between successive signals as represented by the curve is determined, and the interval between the excitation transient and the minimum is determined to provide a measure of the characteristic response of the medium.

2. A method according to claim 1, wherein the excitation transient is an excitation pulse.

3. A method according to claim 1, wherein the characteristic response of the medium is assessed from a single excitation transient.

4. A method according to claim 1, wherein the characteristic response of the medium is assessed by averaging the characteristic response assessed in relation to a series of excitation transients.

5. A method according to claim 1, wherein the signals result from excitation of fluorophores by the excitation.

6. A method according to claim 1, wherein the signals result from energy transfer to one species from another species excited by the excitation.

7. A method according to claim 1, wherein the timing of the signals is determined from a predetermined portion of each signal.

8. A method according to claim 1,
wherein excitation is delivered to a plurality of samples of the medium from a single source, and signals from each sample are received by a single detector.

9. A method according to claim 8, wherein each of the plurality of samples receives an excitation in turn, and signals from each of the samples are detected in turn.

10. A method according to claim 8, wherein each of the plurality of samples receives an excitation simultaneously, and signals from all of the samples are detected in parallel.

11. A method according to claim 1, wherein a property of the excitation is used to normalise the detected signals.

12. A method according to claim 1, wherein a property of the excitation is recorded and subsequently deconvoluted from the detected signals.

13. A method according to claim 1, wherein a bleaching rate of a fluorophore is measured.

14. A apparatus for carrying out a method of assessing the characteristic response of a medium to an excitation transient of predetermined duration which causes the medium to emit a series of signals over a period of time which is long relative to the duration of the excitation transient, wherein the signals are detected, the duration of each interval between successive signals is measured, and a relationship relating to the interval between the excitation transient and the emission of each signal to the interval between each signal and the preceding signal in the series is derived to represent the characteristic response; the apparatus comprising:

means for detecting each of the series of signals, means for measuring the duration of each interval between successive signals in the series, means for plotting the interval between the excitation and the emission of each signal against the interval between each signal and the preceding signal in the series, means for fitting a curve to the plot, means for determining position of the minimum value of the interval between successive signals as represented by the curve, and means for determining the interval between the excitation and the minimum to provide a measure of the characteristic response of the medium.

15. A method for assessing the characteristic response of a medium to an excitation transient of predetermined duration which causes the medium to emit a series of photons over a period of time which is long relative to the duration of the excitation transient, wherein the photons are detected, the duration of each interval between successive photons is measured, and a relationship relating the interval between the excitation transient and the emission of each photon to the interval between each photon and the preceding photon in the series is derived to represent the characteristic response;

wherein the interval between the excitation transient and the emission of each photon is plotted against the interval between each photon and the preceding photon in the series, a curve is fitted to the plot, the position of a minimum value of the interval between successive photons as represented by the curve is determined, and the interval between the excitation transient and the minimum is determined to provide a measure of the characteristic response of the medium.

* * * * *